United States Patent [19]

Manoury et al.

[11] Patent Number: 5,010,079
[45] Date of Patent: Apr. 23, 1991

[54] INDOLONE DERIVATIVES, THEIR PREPARATION AND THEIR APPLICATION IN THERAPY

[75] Inventors: Philippe Manoury, Verrieres le Buisson; Jean Binet, Breuillet; Daniel Obitz, Fontenay aux Roses; Gerard Defosse, Paris; Elisabeth Dewitte, Saint-Gratien; Corinne Veronique, Villejuif, all of France

[73] Assignee: Synthelabo, Paris, France

[21] Appl. No.: 388,373

[22] Filed: Aug. 2, 1989

[30] Foreign Application Priority Data

Aug. 3, 1988 [FR] France .................. 8810482

[51] Int. Cl.$^5$ .............. C07D 401/06; C07D 403/06; A61K 31/47; A61K 31/495
[52] U.S. Cl. .................. 514/253; 514/254; 544/360; 544/362; 544/373; 548/485; 548/486
[58] Field of Search ............ 544/360, 362, 373; 514/253, 254

[56] References Cited

U.S. PATENT DOCUMENTS

| | | | |
|---|---|---|---|
| 3,188,313 | 6/1965 | Archer | 544/373 |
| 3,362,956 | 1/1968 | Archer | 544/373 |
| 3,732,248 | 5/1973 | Canas-Rodriguez et al. | 548/486 |
| 4,883,795 | 11/1989 | Lowe, III et al. | 544/373 |

OTHER PUBLICATIONS

Kulkarni et al. *Drugs of Today*, 24 p. 175 (1988).
Glennon, *J. Med. Chem.* 30 p. 1 (1987).
Taborsky et al., "The Synthesis and Preliminary Pharmacology of Some 9H-Pyrido[3,4-b]indoles (β-Carbolines) and Tryptamines Related to Serotonin and Melatonin", Journal of Medicinal Chemistry, vol. 7, No. 2, Mar. 1964, pp. 135-141.

Primary Examiner—Mukund J. Shah
Assistant Examiner—F. Bernhardt
Attorney, Agent, or Firm—Wegner, Cantor, Mueller & Player

[57] ABSTRACT

An indolone derivative is useful for the treatment of anxiety, depression and schizophrenia and is a 5HT$_{1A}$ agonist and 5HT$_2$ antagonist, which is a compound of formula (I):

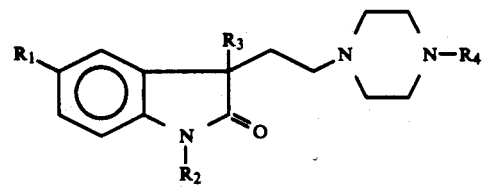

in which
$R_1$ is a hydrogen or halogen atom or a $(C_{1-4})$alkyl radical,
$R_2$ is a hydrogen atom or a $(C_{1-4})$alkyl radical,
$R_3$ is a hydrogen atom, a $(C_{1-4})$alkyl radical or an S-$(C_{1-4})$ alkyl radical; and
$R_4$ is a phenyl, chlorophenyl, naphthyl, 7-methoxy-1-naphthyl, 6-methoxy-1-indanyl, 2-methoxy-6-pyridyl, 3-methoxy-2-pyridyl, isoquinolyl, 7-methoxy-1-isoquinolyl, 7-methoxy-1,2,3,4-tetrahydro-1-naphthyl or 7-fluoro-1-naphthyl radical;
or a pharmaceutically acceptable acid addition salt thereof.

8 Claims, No Drawings

INDOLONE DERIVATIVES, THEIR PREPARATION AND THEIR APPLICATION IN THERAPY

The present invention relates to indolone derivatives, to their preparation and to their application in therapy.

The present invention provides an indolone derivative which is a compound of formula (I):

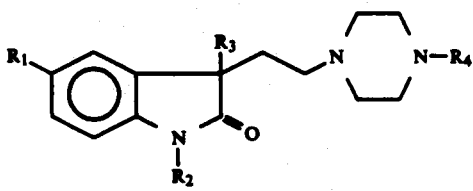

in which
R$_1$ is a hydrogen or halogen atom or a (C$_{1-4}$)alkyl radical;
R$_2$ is a hydrogen atom or a (C$_{1-4}$)alkyl radical;
R$_3$ is a hydrogen atom, a (C$_{1-4}$)alkyl radical or an S-(C$_{1-4}$) alkyl radical; and
R$_4$ is a phenyl, chlorophenyl, naphthyl, 7-methoxy-1-naphthyl, 6-methoxy-1-indanyl, 2-methoxy-6-pyridyl, 3-methoxy-2-pyridyl, isoquinolyl, 7-methoxy-1-isoquinolyl, 7-methoxy-1,2,3,4-tetrahydro-1-naphthyl or 7-fluoro-1-naphthyl radical;
or a pharmaceutically acceptable acid addition salt thereof.

Preferably R$_1$ is a hydrogen, chlorine or fluorine atom or a methyl group; R$_2$ is a hydrogen atom or a methyl group; R$_3$ is a hydrogen atom or a methyl or thioethyl group; R$_4$ is a 3-chlorophenyl or 2-naphthyl group and the salt is a fumarate or maleate salt.

The compounds possess one or more asymmetric carbon atoms. The diastereoisomers and enantiomers of these compounds form part of the invention.

The compounds of the invention may be prepared according to the reaction schemes given in Appendices 1 and 2.

When R$_3$ is H, the compounds may be prepared according to Reaction Scheme 1: a compound of formula (II), 4-R$_1$-benzenamine, in which R$_1$ is as defined above is reacted with tert-butyl hypochlorite, then with 3-ethylthio-γ-butyrolactone (A. F. Wagner, U.S. Pat. No. 2,842,590, CA 52 18220 d) and finally with triethylamine, leading to the compound of formula (III) which is converted to a tosylate which is reacted with a 1-R$_4$-piperazine of formula (IV) in which R$_4$ is as defined above; a compound of formula (V) is then obtained;
which compound is desulphurized directly to obtain the compound of formula (I) in which R$_2$ is H; or
which compound is reacted in the presence of sodium hydride with a compound of formula R$_2$X$_1$ in which X$_1$ is a halogen atom, and the intermediate compound is then desulphurized to obtain the compound of formula (I) in which R$_2$ is a (C$_{1-4}$)alkyl radical.

When R$_3$ is other than H, the compounds may be prepared according to Reaction Scheme 2: A 4-R$_1$-benzenamine of formula (II) is reacted with tert-butyl hypochlorite, then with ethyl 2-ethylthio-2-R$_3$-ethanoate, in which R$_3$ is as defined above, and then with triethylamine, leading to the compound of formula (VI) which is reacted in the presence of sodium hydride with a compound of formula R$_2$X$_2$, in which X$_2$ is a halogen atom, and the intermediate compound is then desulphurized to the compound of formula (VII) which is reacted with a compound of formula (VIII) to obtain the compound of formula (I).

The compounds of formula (II) are described in the literature. The compounds of formula (IV) are described by the Applicant in French Patent Application No. 88/10,481 and its United States counterpart (Ser. No. 388,374) or in European Patent Application No. 89401330.9, Publ. No. 0343050(U.S. Ser. No. 352,342) or in the literature.

The compounds of formula (VIII) are prepared from the compounds of formula (IV) according to conventional methods described in the literature.

The compounds of the invention containing an asymmetric carbon in the radical (CH$_2$)$_2$N=N-R$_4$ can exist in the form of enantiomers which may be prepared by stereospecific synthesis; that is to say, by reaction between a compound of formula (III) and an enantiomer of the piperazine of formula (IV).

Examples 5 and 6 illustrate this preparation.

The Examples which follow illustrate the invention.

The analyses and the IR and NMR spectra confirm the structure of the compounds.

EXAMPLE 1

5-Fluoro-3-{2-[4-(7-methoxy-1,2,3,4-tetrahydro-1-naphthyl)-1-piperazinyl]ethyl}-1,3-dihydro-2(2H)-indolone fumarate

1.1

3-(Ethylthio)-5-fluoro-3-(2-hydroxyethyl)-1,3-dihydro-2(2H)-indolone

A solution of 22.2 g (0.2 mole) of 4-fluoroaniline in 650 ml of methylene chloride is cooled to −65° C. and 21.4 ml of t-butyl hypochlorite, dissolved in 90 ml of CH$_2$Cl$_2$, are then added dropwise. The mixture is stirred for ¼ hour after the addition is complete and 26.2 g (0.2 mole) of 3-(ethylthio)-γ-butyrolactone, diluted in 90 ml of CH$_2$Cl$_2$, are then added in the course of approximately 1 hour.

The mixture is kept stirred at −65° C. for 2 hours and 27.5 ml of triethylamine, diluted in 90 ml of CH$_2$Cl$_2$, are added. The temperature of the mixture is allowed to return to 20° C. and the mixture is left to stand overnight. The reaction mixture is poured into water, settling is allowed to take place, and the organic phase is separated and dried, filtered and evaporated. The resulting solid is purified by chromatography on silica (eluant: ethyl acetate).

3-(Ethylthio)-5-fluoro-3-(2-hydroxyethyl)-1,3-dihydro-2(2H)indolone is obtained.

M.p. 125° C.

1.2

3-(Ethylthio)-5-fluoro-3-(2-hydroxyethyl)-1,3-dihydro-2(2H)-indolone tosylate

A solution of 19 g (0.075 mole) of 3-(ethylthio)-5-fluoro-3-(2-hydroxyethyl)-1,3-dihydro-2(2H)-indolone in 150 ml of pyridine is cooled to approximately 5° C.

15.6 g (0.082 mole) of 4-methylbenzenesulphonyl chloride is then added portionwise.

The temperature of the mixture is allowed to return to 20° C. and the mixture is left standing overnight. The mixture is poured into water, acidified and extracted with CH$_2$Cl$_2$. The organic phase is washed with water, dried, filtered and evaporated.

3-(Ethylthio)-5-fluoro-3-(2-hydroxyethyl)-1,3-dihydro-2(2H)-indolone tosylate is obtained.

M.p. 105° C.

1.3

3-(Ethylthio)-5-fluoro-3-{2-[4-(7-methoxy-1,2,3,4-tetrahydro-1-naphthyl)-1-piperazinyl]ethyl}-1,3-dihydro-2(2H)-indolone.

A mixture of 8.1 g (0.0328 mole) of 1-(7-methoxy-1,2,3,4-tetrahydro-1-naphthyl)piperazine and 6.7 g (0.0164 mole) of 3-(ethylthio)-5-fluoro-3-(2-hydroxyethyl)-1,3-dihydro-2(2H)-indolone is heated to 110° C. for 1 hour.

The mixture is cooled and purified by chromatography on silica (eluant: ethyl acetate/CH$_2$Cl$_2$, 50:50).

An oil is obtained, which is used in the crude state for the next stage of the synthesis.

1.4

5-Fluoro-3-(2-[4-(7-methoxy-1,2,3,4-tetrahydro-1-naphthyl)-1-piperazinyl]ethyl}-1,3-dihydro-2(2H)-indolone fumarate.

4.7 g (0.01 mole) of the above derivative, dissolved in 100 ml of ethanol, is brought to reflux for 2 hours in the presence of 30 g of deactivated Raney nickel.

The nickel is filtered off and rinsed with ethanol and the filtrate is then evaporated.

5-Fluoro-3-{2-[4-(7-methoxy-1,2,3,4-tetrahydro-1-naphthyl)-1-piperazinyl]ethyl}-1,3-dihydro-2(2H)-indolone fumarate is prepared in an ethanol/ether mixture.

M.p. 136° C.

EXAMPLE 2

5-Fluoro-1-methyl-3-(2-[4-(1-naphthyl)-1-piperazinyl]ethyl}-1,3-dihydro-2(2H)-indolone fumarate

2.1

3-Ethylthio-5-fluoro-3-(2-[4-(1-naphthyl)-1-piperazinyl]ethyl}-1,3-dihydro-2(2H)-indolone The product is obtained by following the procedure described under 1.3, starting with 31.6 g (0.148 mole) of 1-naphthylpiperazine and 30.5 g (0.074 mole) of 3-(ethylthio)-5-fluoro-3-(2-hydroxyethyl) -1,3-dihydro-2(2H)-indolone tosylate.

M.p. 174°-175° C.

2.2

3-Ethylthio-5-fluoro-1-methyl-3-{2-[4-(1-naphthyl)-1-piperazinyl]ethyl}-1,3-dihydro-2(2H)-indolone.

3.2 g (0.005 mole) of the above compound, dissolved in 25 ml of DMF, are added to a suspension of 0.25 g (0.0055 mole) of 50% strength NaH in 25 ml of DMF.

When the evolution of hydrogen has ceased, 0.5 ml of methyl iodide is introduced and the mixture is then heated to 50° C. for 2 hours.

The mixture is poured into water and extracted with ether. After the usual treatment, 3-{2-[4-(1-naphthyl)-piperazinyl]ethyl}-3-ethylthio-5-fluoro-1-methyl-1,3-dihydro-2(2H)-indolone is collected in the form of an oil, which is desulphurized using the procedure described under 1.4.

5-Fluoro-1-methyl-3-(2-[4-(1-naphthyl)-1-piperazinyl]ethyl}-1,3-dihydro-2(2H)-indolone fumarate is obtained.

M.p. 198°-200° C.

EXAMPLE 3

5-Fluoro-1,3-dimethyl-3-(2-[4-(1-naphthyl)-1-piperazinyl]ethyl}-1,3-dihydro-2(2H)-indolone.

3.1

3-(Ethylthio)-5-fluoro-3-methyl-1,3-dihydro-2(2H)indolone

The compound is prepared as described under 1.1, starting with 24.4 g (0.22 mole) of 4-fluoroaniline, 26.2 ml of t-butyl hypochlorite and 35.7 g (0.22 mole) of ethyl 2(ethylthio)propanoate.

M.p. 113°-114° C.

3.2

3-(Ethylthio)-5-fluoro-1,3-dimethyl-1,3-dihydro-2(2H)-indolone 11.3 g (0.05 mole) of 3-(ethylthio)-5-fluoro-3-methyl-1,3-dihydro-2(2H)-indolone are methylated as described under 2.2, starting with 2.6 g (0.055 mole) of 50% strength NaH and 3.7 ml of methyl iodide.

M.p. 63°-65° C.

3.3 5-Fluoro-1,3-dimethyl-1,3-dihydro-2(2H)-indolone 20.5 g of the above compound are desulphurized in 150 ml of ethanol under reflux in the presence of 120 g of deactivated Raney nickel.

The compound is obtained in the form of an oil.

3.4

5-Fluoro-1,3-dimethyl-3-{2-[4-(1-naphthyl)-1-piperazinyl]ethyl}-1,3-dihydro-2(2H)-indolone 1.6 g (0.009 mole) of the above compound, dissolved in 10 ml of DMF, are added to a suspension of 0.5 g (0.01 mole) of 50% strength NaH in 20 ml of DMF. When the reaction with sodium is complete, 2.4 g (0.009 mole) of 1-(2-chloroethyl)-4-(1-naphthyl)piperazine, diluted in 10 ml of DMF, are added and the mixture is then heated to 60° C. for 12 hours.

The mixture is poured into water and extracted with ether and the extract is dried, filtered and evaporated.

The product is purified by chromatography on a silica column. 5-Fluoro-1,3-dimethyl-3-{2-[4-(1-naphthyl)-1-piperazinyl]ethyl}-1,3-dihydro-2(2H)-indolone is obtained.

M.p. 144°-146° C.

EXAMPLE 4

5-Fluoro-3-{2-[4-(7-methoxy-1-naphthyl)-1-piperazinyl]ethyl)-1,3-dihydro-2(2H)-indolone

4.1

3-(Ethylthio)-5-fluoro-3-(2-[4-(7-methoxy-1-naphthyl)-1piperazinyl]ethyl)-1,3-dihydro-2(2H)-indolone An intimate mixture of 3.66 g (0.0151 mole) of 1-(7-methoxy-1-naphthyl)piperazine and 3.09 g (0.00755 mole) of 3-(ethylthio)-5-fluoro-3-(2-hydroxyethyl)-1,3-dihydro-2(2H)-indolone tosylate is heated to 130° C. for 45 minutes.

The reaction medium is then stirred between alkaline water and methylene chloride, settling is allowed to take place and the organic phase is separated and then washed and dried over magnesium sulphate.

After evaporation of the solvent, the residual oil is eluted with a methylene chloride/acetone (90:10) mixture on a column of 250 g of Merck 40 silica.

After concentration of the pure fractions, 2.8 g of a white solid are obtained, and this is ground in ether, then drained, washed and dried. 2.3 g of a white solid are finally obtained, the melting point of which is 180°-2° C..

4.2
5-Fluoro-3-{2-[4-(7-methoxy-1-naphthyl)-1-piperazinyl]ethyl}-1,3-dihydro-2(2H)-indolone A suspension of 5 g of the above solid and 50 g of Raney nickel (deactivated beforehand with acetone) is heated under reflux for 3 hours in 350 ml of ethanol. After filtration of the catalyst and evaporation of the solvent, the remaining solid is partially dissolved in 2.2 l of ether. Some insoluble matter is filtered off and the filtrate is concentrated to approximately 60 ml and then left to stand in the refrigerator.

After several hours, the crystallized solid is drained, washed with ether and dried, and 3.27 g of a white solid of melting point 177°-8° C. are obtained.

EXAMPLE 5
5-Fluoro-3-(2-[4-(7-methoxy-1,2,3,4-tetrahydro-1-naphthyl)-1-piperazinyl]ethyl}-1,3-dihydro-2(2H)-indolone fumarate (dextrorotatory isomer)

5.1
3-(Ethylthio)-5-fluoro-3-{2-[4-(7-methoxy-1,2,3,4-tetrahydro-1-naphthyl)-1-piperazinyl]ethyl}-1,3-dihydro-2(2H)-indolone (dextrorotatory isomer)

A mixture of 19.8 g (0.0803 mole) of the dextrorotatory isomer of 1-(7-methoxy-1,2,3,4-tetrahydro-1-naphthyl)piperazine and 16.3 g (0.0398 mole) of 3-(ethylthio)-5-fluoro-3-(2-hydroxyethyl)-1,3-dihydro-2(2H)-indolone tosylate in 140 ml of toluene is brought to the refluxing temperature for 2 h.

The mixture is stirred in the presence of ether and 2N sodium hydroxide. After settling has taken place and separation, the mixture is washed with water, dried and evaporated.

After chromatography on a silica column, using as eluant a $CH_2Cl_2$/methanol mixture from 98:2 to 98:4, 16.2 g of pure product are recovered.

5.2
5-Fluoro-3-{2-[4-(7-methoxy-1,2,3,4-tetrahydro-1-naphthyl)-1-piperazinyl]ethyl}-1,3-dihydro-2(2H)-indolone (dextrorotatory isomer)

106 g of Raney nickel in 700 ml of acetone are brought to the refluxing temperature for 2 h and the mixture is then washed with alcohol.

16 g (0.033 mole) of the compound obtained above, dissolved in 400 ml of ethanol, are then added. The mixture is brought to the refluxing temperature for 2 h. The nickel is filtered off and rinsed with ethanol and the filtrate is evaporated. The compound in base form melts at 114° C.

The fumarate of the compound obtained is prepared in a mixture of ethanol and ether. M.p. 132° C.
$[\alpha]_D^{20} = 78.5°$ c. = 1.04 methanol.

EXAMPLE 6
5-Fluoro-3-{2-[4-(7-methoxy-1,2,3,4-tetrahydro-1-naphthyl)-1-piperazinyl]ethyl}-1,3-dihydro-2(2H)-indolone fumarate (laevorotatory isomer)

6.1
3-(Ethylthio)-5-fluoro-3-{2-[4-(7-methoxy-1,2,3,4-tetrahydro-1-naphthyl)-1-piperazinyl]ethyl}-1,3-dihydro-2(2H)-indolone (laevorotatory isomer)

A mixture of 13.9 g (0.0564 mole) of the laevorotatory isomer of 1-(7-methoxy-1,2,3,4-tetrahydro-1-naphthyl)piperazine, 20.06 g (0.0490 mole) of 3-(ethylthio)-5-fluoro-3-(2-hydroxyethyl)-1,3-dihydro-2(2H)-indolone tosylate and 9.4 g (0.112 mole) of sodium hydrogen carbonate in 155 ml of toluene is brought to 100° C. for 9 h on an oil bath.

The inorganic salts are filtered off and the filtrate is then evaporated.

After chromatography on a silica column with a 97:3 $CH_2Cl_2$/methanol mixture as eluant, 19.4 g of pure product are obtained.
$[\alpha]_D^{20} = -81.5°$.

6.2
5-Fluoro-3-{2-[4-(7-methoxy-1,2,3,4-tetrahydro-1-naphthyl)-1-piperazinyl]ethyl}-1,3-dihydro-2(2H)-indolone (laevorotatory isomer).

127 g of Raney nickel are brought to boiling for 2 h in 850 ml of acetone. The acetone is separated after settling has taken place and washed twice with ethanol.

A solution of 19.3 g (0.04 mole) of the compound obtained above in 480 ml of absolute ethanol is added to this mixture. The mixture is brought to the refluxing temperature for 1 h while stirring vigorously.

The Raney nickel is filtered off, the filtrate is evaporated under vacuum and the mixture is taken up with ether. Some insoluble matter is filtered off. After evaporation, the product is obtained in base form.

The fumarate of this compound is prepared in an ethanol/ether mixture.

After recrystallization in propanol, the product melts at 132° C.
$[\alpha]_D^{20} = -78.3°$ c. = 1.04 methanol.

The compounds of the invention prepared by way of examples are illustrated in the table which follows.

TABLE

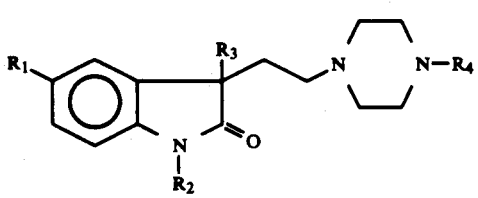

(I)

| Compound | $R_1$ | $R_2$ | $R_3$ | $R_4$ | M.p. (°C.) |
|---|---|---|---|---|---|
| 1 | H | H | $SC_2H_5$ | 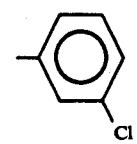 | 116–118 |

TABLE-continued

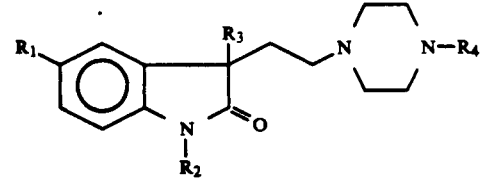
(I)

| Compound | R₁ | R₂ | R₃ | R₄ | M.p. (°C.) |
|---|---|---|---|---|---|
| 2 | H | H | H | 3-chlorophenyl | 173–174 |
| 3 | H | H | SC₂H₅ | 1-naphthyl | 188–192 |
| 4 | H | H | H | 1-naphthyl | 192–194 |
| 5 | H | H | H | phenyl | 146–148 |
| 6 | F | H | SC₂H₅ | 1-naphthyl | 174–175 |
| 7 | F | H | H | 1-naphthyl | 180–183 |
| 8 | F | H | SC₂H₅ | 2-methoxy-1-naphthyl | 180–182 |

TABLE-continued

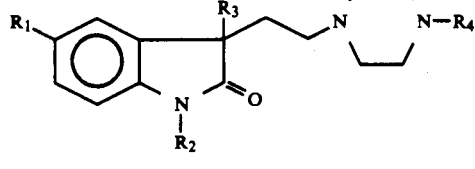
(I)

| Compound | R₁ | R₂ | R₃ | R₄ | M.p. (°C.) |
|---|---|---|---|---|---|
| 9 | F | H | H | 2-methoxy-1-naphthyl | 176–178 |
| 10 | F | H | H | 6-methoxy-indanyl | 177–178 (fumarate) |
| 11 | F | H | H | 6-methoxy-tetrahydronaphthyl | 136 (fumarate) |
| 12 | Cl | H | SC₂H₅ | 1-naphthyl | 193–195 |
| 13 | Cl | H | H | 1-naphthyl | 213–218 |
| 14 | CH₃ | H | SC₂H₅ | 1-naphthyl | 169–171 |
| 15 | F | CH₃ | H | 1-naphthyl | 198–200 (fumarate) |

TABLE-continued (I)

Structure: R1-substituted indolin-2-one with R2 on N, R3 on C3, and C3 bearing -CH2CH2-N(piperazine)N-R4

| Compound | R1 | R2 | R3 | R4 | M.p. (°C.) |
|---|---|---|---|---|---|
| 16 | F | CH3 | CH3 | 2-methylnaphthyl | 144–146 |
| 17 | F | H | H | 6-methyl-2-methoxypyridin-yl | 120 |
| 18 | F | H | H | 2-methyl-3-methoxypyridinyl | 210 (fumarate) |
| 19 | F | H | H | 7-methoxyisoquinolin-1-yl | 214–216 (fumarate) |
| 20 | F | CH3 | H | 7-methoxynaphthyl | 179–181 (fumarate) |
| 21 | F | H | H | 7-methoxyisoquinolinyl | 222–224 (fumarate) |
| 22 | F | CH3 | H | 7-methoxy-1,2,3,4-tetrahydronaphthyl | 166–168 (maleate) |
| 23 | F | H | H | 7-methoxy-1,2,3,4-tetrahydronaphthyl | dextrorotatory isomer 132 fumarate |
| 24 | F | H | H | 7-methoxy-1,2,3,4-tetrahydronaphthyl | laevorotatory isomer 132 fumarate |
| 25 | F | H | SC2H5 | 6-fluoronaphthyl | 201–2 |
| 26 | F | H | H | 6-fluoronaphthyl | 187–9 |

The compounds of the invention were subjected to a series of pharmacological tests which demonstrated their value as substances having therapeutic activity.

Thus, they were subjected to a study in respect of their affinity for 5-HT$_1$A type serotoninergic receptors. In the rat hippocampus, the compounds displace a labelled specific ligand, [$^3$H]-8-hydroxy-2-dipropylaminotetralin (hereinafter designated "[$^3$H]-8-OH-DPAT"), described by Gozlan et al., Nature, (1983), 305, 140–142.

The animals used are Sprague-Dawley male rats weighing 160 to 200 g. After decapitation, their brain is removed and the hippocampus excised. The tissue is ground in an Ultra-Turrax Polytron apparatus for 30 s at half the maximum speed in 10 volumes of 50 mM Tris buffer whose pH is adjusted to 7.4 with hydrochloric acid (equivalent to 100 mg of fresh tissue per ml). The homogenized tissues are washed three times at 4° C. by centrifuging them on each occasion at 48,000×g and resuspending the pellet for 10 min in cooled fresh buffer. Finally, the last pellet is suspended in the buffer to produce a concentration of 100 mg of original tissue per ml of 50 mM buffer. The suspension is then left to incubate at 37° C. for 10 min.

The binding with [$^3$H]-8-OH-DPAT is determined by incubating 10 μl of membrane suspension in a final volume of 1 ml of buffer containing 10 μM pargyline.

After incubation, the membranes are recovered by filtration on Whatman GF/B filters, which are washed three times with 5-ml aliquot portions of ice-cold buffer. The filters are extracted in scintillation fluid and their radioactivity is measured by liquid scintigraphy. The specific binding of [$^3$H]-8-OH-DPAT is defined as the quantity of radioactivity retained on the filters and capable of being inhibited by coincubation in 10 μM 5-hydroxytryptamine. At a [$^3$H]-8-OH-DPAT concentration of 1 nM, the specific binding represents from 70 to 80% of the total radioactivity recovered on the filter.

For each concentration of test compounds, the percentage inhibition of the binding with [$^3$H]-8-OH-DPAT, and then the IC$_{50}$ concentration, the concentration which inhibits 50% of the binding, are determined.

For the compounds of the invention, the IC$_{50}$ values lie from 0.001 to 0.3 μM.

The central activity of the compounds of the invention was assessed by their effects on the "PGO (pontogeniculooccipital) spikes" induced by reserpine (PGO-R test) in cats, according to the method described by H. Depoortere, Sleep 1976, 3rd Europ. Congr. Sleep Res., Montpellier 1976, 358-361 (Karger, Basel 1977).

Cumulative doses of test compounds are administered from 0.01 to 3 mg/kg intravenously) at 30-min time intervals, 4 h after the intraperitoneal injection of a dose of 0.75 mg/kg of reserpine, to curarised cats under artificial ventilation. The electroencephalographic and phasic (PGO-R spike) activities are obtained using cortical and deep (lateral geniculate) electrodes. For each dose of test compound, the percentage decrease in the number of PGO spikes, and then the AD$_{50}$, the active dose which decreases this number of spikes by 50%, are determined.

For the compounds of the invention, the intravenous AD$_{50}$ values lie from 0.001 to 1 mg/kg.

The results of the tests show that some of the compounds of general formula (I) possess a high affinity and a high selectivity for 5-HT$_{1A}$ type serotoninergic receptors. In vivo, they show either an agonist or a partial agonist or an antagonist activity in respect of these receptors.

Some compounds of the invention possess, in addition, an antiserotonin activity in respect of the 5HT2 type receptors.

This activity was demonstrated "in vitro" by the displacement of ligands bound specifically to serotoninergic receptors (SBS binding test), and "in vivo" by antagonism of the effects of serotonin at peripheral level (OES test) and at central level (AHT test). SBS Test: the compounds of the invention were subjected to a test of displacement of the binding of spiroperidol to the serotoninergic (5-HT2) receptors of rat cerebral cortex.

For this test, rat brains are removed and the cortex is dissected out and homogenized at 0° C. in 10 volumes of a mixture containing, per liter, 50 millimoles of Tris/HCl buffer at pH 7.4, 120 millimoles of sodium chloride and 5 millimoles of potassium chloride. The homogeneous mixture is centrifuged at 40,000×g for 10 min, and the pellet is then recovered, washed by suspending it in the same buffer mixture, homogenized again and centrifuged, repeating this treatment of the pellet a second time Lastly, the final pellet is diluted in the same buffer mixture on the basis of 100 mg of wet tissue per ml of buffer.

The tissue is then subjected to a prior 10-min incubation at 37° C. in the presence of 10 micromoles/l of pargyline, and then to a 20-min incubation at 37° C. in the presence of [$^3$H]spiroperidol (specific activity: 25.6 Ci per millimole) at a concentration of 0.3 nanomole/l and test compound at concentrations ranging from 0.0001 to 100 micromoles/l.

1-ml aliquots are removed and filtered under vacuum, and the filters are washed twice with 5 ml of cold buffer and dried. The radioactivity is measured in toluene in the presence of 5 g/l of 2,H-diphenyloxazole (PPO) and 0.1 g/l of 1,4-bis(5-phenyl-2-oxazolyl)benzene (POPOP).

To assess the activity of the compounds, the curve is plotted for the percentage inhibition of the specific binding of [$^3$H]spiroperidol as a function of the concentration of displacing drug. The IC$_{50}$ concentration, the concentration which inhibits 50% of the specific binding, is determined graphically.

The specific binding is defined as the binding displaced by 100 micromoles/l of 5-HT.

The IC$_{50}$ concentrations of the compounds of the invention lie for the most part from 1 to 50 nanomoles/l. OES Test: the antiserotoninergic activity of the compounds of the invention was also demonstrated by their effect on serotonin-induced oedema in rats, according to the method described by Maling et al., J. Pharmacol. Exp. Therap., 191 (2), 300-310 (1974).

The animals are CD strain male rats (Ch. River, France) weighing 120 to 150 g, fasted for 18 h and distributed in randomized sets.

The compounds, dissolved or suspended in Tween 80® at a concentration of 1%, are administered orally on the basis of 0.5 ml per 100 g of bodyweight, 1 h before the sub-plantar injection of 1 μg of serotonin (dissolved in sterile physiological saline, in a volume of 0.1 ml) into one of the hind legs. The volume of the oedema is measured 1 h after the injection of serotonin by means of an Ugo Basile mercury plethysmometer. The AD$_{40}$ (dose which decreases by 40% the volume of the oedema, relative to the control animals) is determined graphically.

The AD$_{40}$ of the compounds of the invention, determined orally, is from 0.1 to 2 mg/kg. AHT Test: the antiserotoninergic activity of the compounds was studied in respect of their effect on the antagonism of "head twitches" induced by L-5-hydroxy-tryptophan (L-5-HTP) in mice, according to the method described by Corne et al., Br. J. Pharmacol., 20, 106-120 (1962).

The mice (CDI males, Charles River France; 18-22 g of bodyweight) receive the test products at increasing doses, or the solvent, intraperitoneally or orally, simultaneously with (i.p. administration) or sixty minutes before (oral administration) a subcutaneous injection of L-5-HTP at a dose of 250 mg/kg. Forty-five minutes after this injection of 5-HTP, the number of twitches is counted, for each mouse, for one minute.

For each treatment, the mean number of twitches, as well as the percentage change relative to the control batch, are calculated.

From the dose-response curve, the AD50 (50% active dose or dose which decreases by 50% the mean number of twitches relative to the control animals) is determined by the graphic method of Miller and Tainter (Proc. Soc. Exp. Biol. Med., (1944), 57, 261).

The $AD_{50}$ values of the compounds of the invention lie from 0.05 to 2 mg/kg when administered intraperitoneally and between 0.1 and 4 mg/kg when administered orally.

The compounds of the invention are useful for the treatment of migraine, anxiety, depression, obesity, schizophrenia, vascular or gastrointestinal spasms, hypertension and platelet aggregation, and as antiemetics.

The compounds of the invention may be administered orally or parenterally, in combination with any suitable excipient.

The daily dosage can range from 1 to 1,000 mg.

SCHEME 1
APPENDIX 1

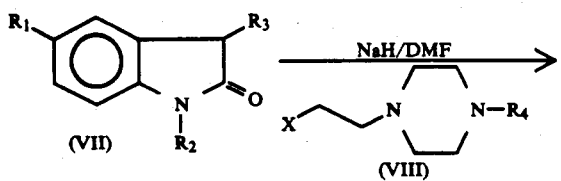

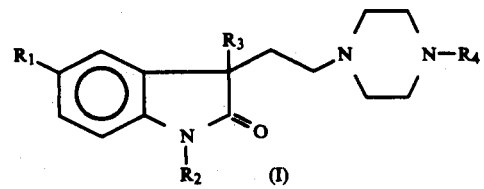

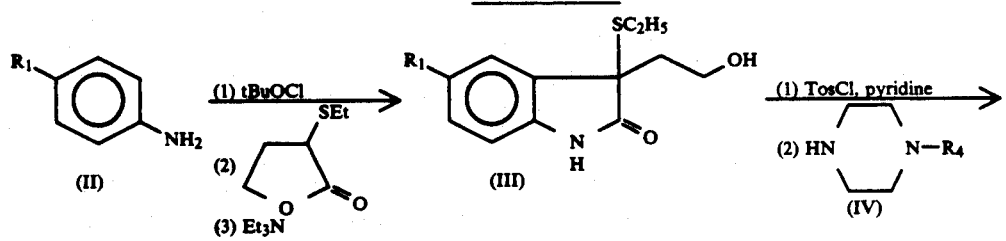

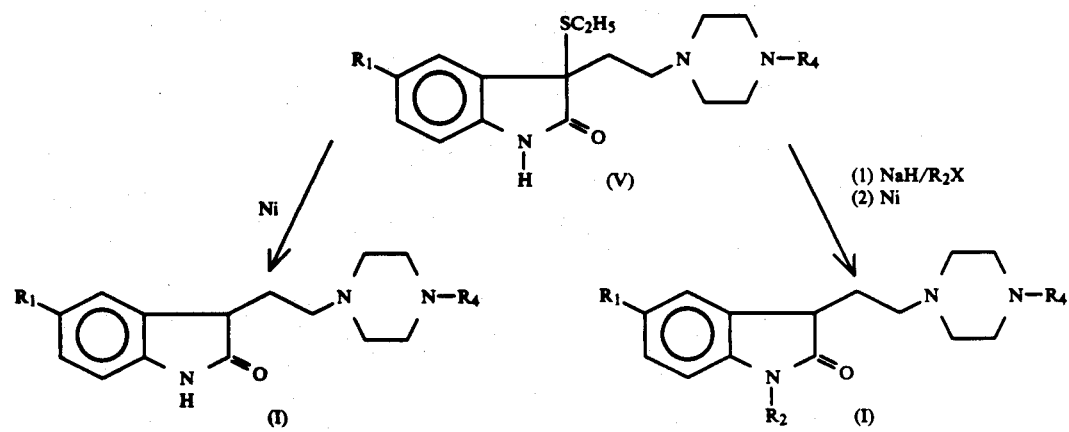

SCHEME 2
APPENDIX 2

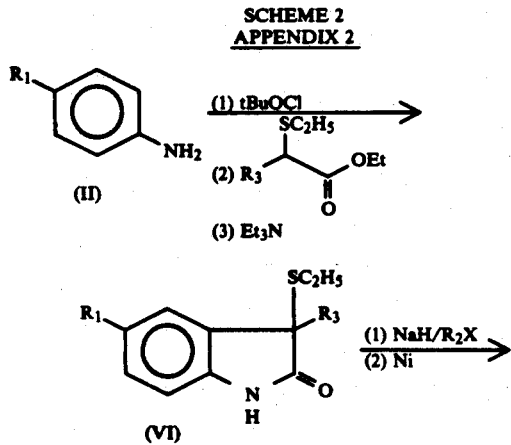

EXAMPLE 1A 1-(7-Methoxy-1-naphthalenyl)piperazine 32 g (0.184) of 7-methoxy-1-naphthalenamine (Helv. Chim. Acta. 30 816–38, 1947) and 32.84 g (0.184 mol) of bis-(2-chloroethyl)amine hydrochloride in solution in 170 ml of butanol are placed in a 500 ml flask, surmounted by a Dean-Stark water separator, provided with a magnetic stirrer and placed under an argon atmosphere. A spatula-point of potassium iodide is added and the reaction mixture is heated to reflux temperature for 20 h. Then 11.6 g (0.092 mol) of potassium carbonate is added and the mixture left to reflux for 10 h. A further 3.87 g (0.03 mol) of the same reagent is added and the mixture left to reflux for a further 8 h. This operation is repeated twice. The reaction mixture is evaporated to dryness and the residue triturated between water and ether; a mauve solid is centrifuged out. 39.2 g (88%) of the hydrochloride of the product is thus obtained.

The base is liberated by stirring the hydrochloride in water, in the presence of 20 ml of 10N caustic soda, and the mixture is extracted with ether. After drying and evaporation of the solvent, the crude oil is distilled, bp (0.1 mm Hg)=about 200° C.

25.5 g (57.2%) of a colourless oil is finally obtained, the NMR spectrum of which confirms its structure.

The fumarate of this base is prepared, and a white solid is obtained; mp 189°-191° C.

EXAMPLE 2A (±)1-(7-methoxy-1,2,3,4-tetrahydro-1-naphthalenyl)-piperazine

1-Chloro-7-methoxy-1,2,3,4-tetrahydronaphthalene 35.6 g (0.2 mol) of 7-methoxy-1,2,3,4-tetrahydro-1-naphthalenol (D. G. Thomas, A. H. Nathan J. Am. Chem. Soc. 79, 331, 1948) are stirred at ambient temperature for 3 hours in a liter of concentrated hydrochloric acid.

The mixture is extracted with hexane, the organic phase is washed with water, dried with magnesium sulphate, filtered and evaporated.

37.7 g (96%) of an oil is obtained, which is used in the crude state for the following reaction.

1,1-Dimethylethyl-4-(7-methoxy-1,2,3,4-tetrahydro-1-naphthalenyl)piperazinecarboxylate A mixture of 37.7 g (0.19 mol) of the above product and 29.8 g (0.16 mol) of 1,1-dimethylethyl piperazine-carboxylate (L. A. Carpino et coll. J. Org. Chem. 48, 664, 983) and 55.2 g (0.4 mole) of potassium carbonate in 200 ml of acetone is heated to reflux temperature.

Reflux is maintained for 72 h. The mixture is evaporated, the residue is taken up in water and ether, and then decanted. The ethereal phase is dried, filtered and evaporated. The product is purified by chromatography on a silica column. 38.9 g of oil (70%) is thus obtained.

(±)
1-(7-Methoxy-1,2,3,4-tetrahydro-1-naphthalenyl)-piperazine 39.6 g (0.11 mol) of 1,1-dimethylethyl-7-methoxy-4-(1,2,3,4-tetrahydro-1-naphthalenyl)piperazinecarboxylate in 240 ml of 3 N hydrochloric acid are heated at 45° C. for 2 hours.

The mixture is extracted with ether. The aqueous phase is alkalinized; the base is extracted into ether. The ether phase is dried, filtered and evaporated.

21 g (75%) of oil is obtained from which the fumarate is prepared; mp=176° C.

EXAMPLE 3A (+)1-(7-Methoxy-1,2,3,4-tetrahydro-1-naphthalenyl)-piperazine 81g (0.33 mol) of (±) 1-(7-methoxy-1,2,3,4-tetrahydro-1-naphthalenyl)piperazine is dissolved while warming in 150 ml of ethanol and 50 g of R(−)mandelic acid. The solution is left to cool and then the precipitate is filtered off.

It is recrystallized from ethanol twice. (+)1-(7-methoxy-1,2,3,4-tetrahydro-1-naphthalenyl)piperazine R(−)mandelate is obtained, mp=174° C., $[\alpha]_D^{20}= +56.1°$, c.=2 $CH_3OH$. The salt is converted to an oily base $[\alpha]_D^{20}= +153.0°$, c=14.25 $CH_3OH$.

EXAMPLE 4A (−)1-(7-Methoxy-1,2,3,4-tetrahydro-1-naphthalenyl)-piperazine.

The preceding ethanolic filtrate (ex. 4) is evaporated, and the residue is taken up in water; the aqueous phase is alkalinized and extracted with ether. The ethereal phase is washed, dried, filtered and evaporated. The oil obtained is dissolved in 90 ml of ethanol and 30 g of S(+)mandelic acid while warming. The mixture is left to cool, and the precipitate is filtered. After two recrystallizations from ethanol, (−)1-(7-methoxy-1,2,3,4-tetrahydro-1-naphthalenyl)piperazine S(+)mandelate is obtained; mp=174° C., $[\alpha]_D^{20}= -58.15°$, c=2$CH_3OH$. For the base $[\alpha]_D^{20}= -153.30$ c=14.25 $CH_3OH$.

We claim:

1. An indolone derivative which is a compound of formula (I):

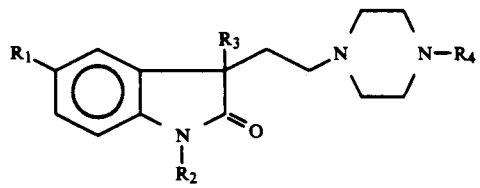

in which $R_1$ is a hydrogen or halogen atom or a $(C_{1-4})$alkyl radical, $R_2$ is a hydrogen atom or a $(C_{1-4})$alkyl radical, $R_3$ is a hydrogen atom, a $(C_{1-4})$alkyl radical or an S-$(C_{1-4})$ alkyl radical; and $R_4$ is a phenyl, chlorophenyl, naphthyl, 7-methoxy-1-naphthyl, 6-methoxy-1-indanyl, 2-methoxy-6-pyridyl, 3-methoxy-2-pyridyl, isoquinolyl, 7-methoxy-1-isoquinolyl, 7-methoxy-1,2,3,4-tetrahydro-1-naphthyl or 7-fluoro-1-naphthyl radical;

or a pharmaceutically acceptable acid addition salt thereof.

2. A compound according to claim 1 in which $R_1$ is a hydrogen, chlorine or fluorine atom or a methyl group.

3. A compound according to claim 1 in which $R_2$ is a hydrogen atom or a methyl group.

4. A compound according to claim 1 in which $R_3$ is a hydrogen atom or a methyl or thioethyl group.

5. A compound according to claim 1 in which $R_4$ is a 3-chlorophenyl or 2-naphthyl group.

6. A compound according to claim 1 in the form of a fumarate or maleate salt.

7. A method of treatment of anxiety, depression, or schizophrenia, which comprises administering to a subject suffering or liable to suffer therefrom an effective amount of a compound as defined in claim 1.

8. A pharmaceutical composition for the treatment of anxiety, depression, and schizophrenia comprising an effective amount of a compound as defined in claim 1 and a pharmaceutically acceptable excipient.

* * * * *